(12) United States Patent
Court et al.

(10) Patent No.: US 7,262,179 B2
(45) Date of Patent: Aug. 28, 2007

(54) WOUND CARE COMPOSITIONS

(75) Inventors: Andrew D. Court, Neston (GB); David D. Kershaw, Neston (GB)

(73) Assignee: Bristol-Myers Squibb Company, New York, NY (US)

( * ) Notice: Subject to any disclaimer, the term of this patent is extended or adjusted under 35 U.S.C. 154(b) by 151 days.

(21) Appl. No.: 10/447,062

(22) Filed: May 28, 2003

(65) Prior Publication Data

US 2004/0242535 A1    Dec. 2, 2004

(51) Int. Cl.
*A01N 43/04* (2006.01)
*A61K 31/70* (2006.01)
*C07H 1/00* (2006.01)

(52) U.S. Cl. .................. 514/54; 514/886; 514/887; 514/944; 536/18.7; 536/52; 536/114; 536/123.1

(58) Field of Classification Search .............. 536/18.7, 536/52, 114, 123.1; 514/54, 886, 887, 944
See application file for complete search history.

(56) References Cited

U.S. PATENT DOCUMENTS

| | | | | |
|---|---|---|---|---|
| 5,578,661 A | * | 11/1996 | Fox et al. | 524/27 |
| 6,136,334 A | | 10/2000 | Viegas et al. | |
| 6,453,608 B1 | | 9/2002 | Flanagan et al. | |
| 6,596,704 B1 | * | 7/2003 | Court et al. | 514/54 |
| 6,635,282 B1 | * | 10/2003 | Flanagan et al. | 424/479 |

FOREIGN PATENT DOCUMENTS

WO    PCT/EP94/02536    2/1995

* cited by examiner

*Primary Examiner*—Patrick Lewis
(74) *Attorney, Agent, or Firm*—John M. Kilcoyne

(57) ABSTRACT

Compositions for the treatment of wounds and skin injuries are described. The compositions, which include gellan gum, increases in viscosity once applied to the wound to form an immobile gel. The composition may be in sprayable form or dispersed in an aqueous solution. Methods of making and using the compositions are also described.

7 Claims, 1 Drawing Sheet

WOUND CARE COMPOSITIONS

This application claims the benefit of priority of United Kingdom Patent Application No. GB 0015682.8, filed on Jun. 28, 2000, the entire contents of which are herein incorporated by reference.

FIELD OF THE INVENTION

This invention relates to compositions for the treatment of wounds or other skin injury.

BACKGROUND OF THE INVENTION

A variety of gels and ointments are available for application to wounds for a variety of purposes. They may, for example, be used to clean a wound, to promote healing of the wound or to prevent infection. In certain circumstances, the gel or ointment may include an active ingredient which is administered to the patient by topical application of the gel or ointment.

One example of a commercially available wound gel is Intrasite® produced by Smith and Nephew Ltd. This gel contains hydrated carboxymethyl cellulose as a main ingredient and is packaged and applied to wounds in gel form as a primary treatment in order to debride the wound. The gel may also assist in preventing the wound from drying out, thereby promoting healing.

Wound gels are generally in gel form at the time of application to the wound and are usually applied by being squeezed from a tube or other suitable container by hand or by other suitable means. Since gels are mobile they offer the advantage of intimate contact with the often irregular surface of a wound, something that is often not achieved with a more rigid wound dressing. The advantage of good contact is however tempered by the conflicting needs of making the gel sufficiently mobile that it can be applied to the wound but not so mobile that it runs out of the wound under the influence of gravity. Gels currently in use suffer from the disadvantage that they can run out of the wound. Thus, there is a need in the art for a composition for topical application to a wound which forms an immobile gel when in contact with the wound or skin injury.

SUMMARY OF THE INVENTION

Figure 1:
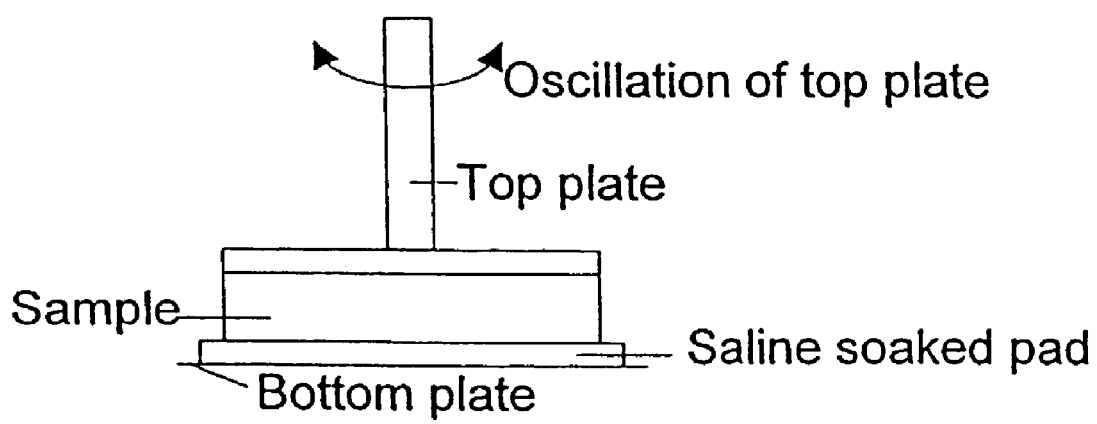
FIG. 1 is a schematic of a parallel plate used in measuring viscosity.

The present invention is directed to a composition for the treatment of a wound or skin injury. The inventive composition comprises between 0.25% to 1.5% by weight of the composition of a gellan gum. In preferred embodiments, the composition can comprise from 0.5% to 1.0% of gellan gum by weight of the composition.

The viscosity of the composition increases once applied to a wound so that an immobile gel is formed. Prior to application to the wound, the composition can be in sprayable form and/or in a spray device which, on actuation, discharges a metered dose of the composition. The composition can also comprise an active ingredient dissolved or dispersed in the composition. The active ingredient can be dissolved or dispersed in an aqueous solution of gellan gum. In preferred embodiments, the active ingredient is selected from the group consisting of hyaluronic acid, esterified hyaluronic acid, an antiseptic, an antifungal agent, an antibacterial agent, and mixtures thereof. In some embodiments, the active ingredient is present in an amount of 0.1 to 10% by weight of the composition.

Preferably, the viscosity of the inventive composition is between 0.1 to 12 Pas, prior to application to the wound. Also preferably, the composition develops a viscosity of from 13 Pas to 800 Pas once in contact with the wound.

Also included in the present invention are methods for treating wounds using the inventive composition.

Still further included in the present invention is an apparatus for forming an immobile gel dressing on wound or skin injury, the apparatus comprising a composition comprising from 0.25% to 1.5% by weight of the composition of a gellan gum, a vessel containing the composition, and a dispensing means in fluid connection with the composition so that the composition can be applied to the wound or skin injury.

Yet still further included in the present invention are methods of forming an in situ immobile gel on a wound or skin injury. These methods comprise dispensing an effective amount of a composition on the wound or skin injury, so that the viscosity of the composition increases and forms an immobile gel. In preferred methods, the composition is 0.25% to 1.5% gellan gum as measured by weight of the composition. In some embodiments, the method includes a dispensing step which comprises spraying, painting or squirting the composition on the wound or skin injury.

DETAILED DESCRIPTION OF THE INVENTION

We have found that it is possible to make a composition for topical application to a wound which forms an immobile gel once in contact with the wound or skin injury.

Accordingly, the invention provides a composition for the treatment of a wound or skin injury comprising from 0.25% to 1.5% by weight of the composition of a gellan gum, said composition forming an immobile gel once in contact with the wound or skin injury.

This gives the advantage that the composition can be applied in a mobile state to give intimate contact with the wound but forms an immobile gel once in contact with the wound reducing the tendency for the gel to run out of the wound. Such a composition is particularly suitable for administering active ingredients to a wound.

Preferable the composition is in sprayable form prior to application to the wound. This offers ease of application of the composition which once applied to the wound forms an adherent cohesive mass.

The composition may be a solution in water or a mixture of water together with another water-miscible solvent, such as propylene glycol.

By the term, "gellan gum" as used herein, is meant the extracullarly produced gum made by processes well known in the art. Gellan gum is composed of sugar monomer units linked-together to form long chains of the individual sugar or monosaccharide units. Particularly preferred is gellan gum described in Carbohydrate Polymers, Vol. 30, 1996: SPECIAL ISSUE, GELLAN GUM: STRUCTURES, PROPERTIES AND FUNCTIONS. Ed. Nishinari K., Pub. Elsevier Science 1996 and "Physicochemical properties of Gellan gum in gel and solution." Author Tsiami Amalia A. Pub. University of East Anglia 1994.

While not wishing to be bound by theory it is believed that gellan gum forms a gel once applied to a wound because molecular association of the saccharide repeat units is promoted due to exposure of the gum to cations contained in the wound and wound exudate.

While many polysaccharides form gel structures it tends to be under specific circumstances, for example the gelation of Carrageenas is sensitive to the ion type e.g. gelling with potassium but not sodium. Glycuronans e.g. alginate gel in the presence of divalent cations but not monovalent cations. Xanthan gum will gel with divalent cations but only at high pH's. Pectic materials gel on cooling if completely esterified or in the presence of divalent cations if incompletely esterified. However Gellan gum is not specific and forms a gel with almost all cations. Suprisingly we have found that gellan gum gels at the relatively low ion concentrations found in a wound environment in contrast to other polysaccharides.

The composition preferably comprises an active ingredient. The term "active ingredient" is used herein to refer to any agent which affects the metabolism or any metabolic or cellular process of the patient (including growth factor nutrients and living cells), promotes cleaning of the wound, combats infection, hypergranulation, inflammation and/or aids in healing. One advantage of delivering the active ingredient in this way is that gellan gums may provide controlled release of active ingredients.

Active ingredients may include other polysaccharides such as hyaluronic acid, salts of hyaluronic acid, esters of hyaluronic acid and hydrocolloids such as sodium carboxymethyl cellulose, pectin and alginate, antiseptic agents such as povidone iodine, antifungal agents such nystatin and Econazole nitrate and antibacterial agents as polymyxin, metronidazole and silver sulphadiazine.

For administration to a patient the composition of the invention may be placed in an apparatus. In a further aspect the invention provides an apparatus for forming an immobile gel dressing on a wound or skin injury, the apparatus comprising:
 a) a composition comprising from 0.25% to 1.5% by weight of the composition of a gellan gum;
 b) a vessel containing the composition; and
 c) a dispensing means in fluid connection with the composition so that the composition can be applied to the wound or skin injury.

The apparatus may be adapted to spray the composition and may be a container fitted with a mechanical pump or a container pressurized with a propellant, for example a conventional aerosol propellant such as nitrogen or a hydrocarbon. The spray device preferably discharges a metered dose of the composition on actuation. In general the metered dose may be up to 0.2 g per actuation.

The composition prior to application to a wound preferably has a viscosity of between 0.1 Pas 12 Pas as measured by a Carrimed CSL 100 Rheometer at 35.5° C. and 1 Hz.

Compositions with these viscosities have been found particularly suitable for application by spraying. Once delivered to the wound the composition develops into a gel that has a viscosity typically of from 13 Pas to 800 Pas after a period of from 0.5 to 40 minutes.

The invention is illustrated by the following Examples in which parts are by weight.

EXAMPLES

Sprayable gel compositions for the treatment of wounds were prepared by mixing gellan gum (Kelcogel F low acyl content ex Kelco Nutrasweet) with propylene glycol, buffered to pH 7 using a phosphate buffer solution as described in the US Pharmacopoeia 1990 (9% by weight of total weight of gel), water and sodium hyaluronate to yield the following compositions.

| | Composition/% w/w | | | | |
|---|---|---|---|---|---|
| Example No | Gellan Gum | Propylene Glycol | Buffer pH 7.0 | Water | Sodium Hyaluronate |
| 1 | 0.80 | 15 | 9 | 75.10 | 0.1 |
| 2 | 0.80 | 15 | 9 | 74.70 | 0.5 |

The time to gel onset and viscosity of the compositions was measured using a rheometer. A sample of the composition is injected on to a pad soaked in 0.9% w/w saline placed on the bottom plate of a parallel pair (see FIG. 1.). A sufficient volume of sample is injected into the space between the plates so as to be in contact with the top plate and the saline soaked pad. During the experiment the force required to rotate the top plate of the pair by a small angle is measured. The movement of the top plate is in the form of a small amplitude oscillation.

When the distance moved by the plate and the force required to oscillate the plate are plotted, the two curves are displaced from each other. This displacement may be measured in degrees and is termed the phase angle. For an ideal liquid this angle is 90° and for a solid it is 0° and for most real materials it is somewhere between the two extreme values. During the gelation process for the gellan materials this phase angle is observed to rapidly fall and then the rate of change reduces. This is associated with an increase in viscosity and is taken as the time at which the gelation starts for these examples. As the solution becomes less able to flow the phase angle falls and the material starts to behave as a conventional solid. This process continues for a considerable time after the onset of gelation, as the system approaches its new equilibrium conformation. The time taken for the gel onset to occur, the viscosity of the solution and the stiffness of the final gel are dependent on the concentrations of the ions present and their type (sodium, potassium, calcium etc.), temperature, and the composition of the gel solution.

The following parameters were set.

| | |
|---|---|
| Plate diameter and type | 4 cm diameter acrylic |
| Plate spacing | 2.500 mm |
| Test frequency | 1 Hz |
| Temperature | 35.5° C. |
| Controlled variable | Displacement |
| Applied amplitude | 1.250 × 10-3 rad. |
| Pad | Paper 68 to 72 gsm |
| Pad size | 5 cm by 5 cm |
| Pad fluid handling | 8 g per g to 9 g per g |

The sample to be tested was heated in a water batch to 35.5° C. A 5 cm by 5 cm minimum square of the pad material was soaked in 0.9% saline and placed on the lower heated platen of the rheometer and readings started.

After the first two data points have been established the sample to be tested is injected into the gap between the top plate of the rheometer and the pad. This is the initial time of the experiment. The experiment is allowed to continue for 45 minutes.

Gel onset is the first point of inflection after the sample was introduced in the phase angle/time plot. The results were as follows:

Viscosity of the compositions as they cure.

TABLE 1

Viscosity data for example 1

| Example 1 | Time to gel onset/s | Viscosity/Pa·s | | | Viscosity of gel/Pa·s | | | | | |
|---|---|---|---|---|---|---|---|---|---|---|
| | | At gel | | | | | | | | |
| | | Initial | onset | Increase % | Initial | 5 min | 10 min | 15 min | 20 min | 40 min |
| | 15 | 3.23 | 4.22 | 31 | 3 | 11 | 95 | 313 | 375 | 738 |
| | 55 | 4.38 | 6.25 | 43 | 4 | 15 | 142 | 395 | 581 | 962 |
| | 59 | 8.13 | 10.63 | 31 | 8 | 17 | 112 | 268 | 408 | 794 |
| Average | 43 | 5.3 | 7.0 | 35 | 5.00 | 13.00 | 116.33 | 325.33 | 454.67 | 831.05 |
| St dev | 24 | 2.6 | 3.3 | 7 | 2.65 | 2.83 | 23.80 | 64.39 | 110.65 | 116.37 |

TABLE 2

Viscosity data for example 2

| Example 2 | Time to gel onset/s | Viscosity/Pa·s | | | Viscosity of gel/Pa·s | | | | | |
|---|---|---|---|---|---|---|---|---|---|---|
| | | At gel | | | | | | | | |
| | | Initial | onset | Increase % | Initial | 5 min | 10 min | 15 min | 20 min | 40 min |
| | 47 | 8.1 | 11.2 | 38 | 8 | 19 | 92 | 144 | 165 | 340 |
| | 63 | 12.0 | 16.7 | 39 | 12 | 22 | 78 | 113 | 145 | 291 |
| | 65 | 15.6 | 20.6 | 32 | 16 | 31 | 101 | 145 | 145 | 391 |
| Average | 58 | 11.9 | 16.2 | 37 | 12.00 | 20.50 | 90.33 | 134.00 | 153.50 | 340.67 |
| St dev | 10 | 3.8 | 4.7 | 4 | 4.00 | 2.12 | 11.59 | 18.19 | 12.02 | 50.00 |

The initial gelation process is the start of a chain of events which changes the gel solution from a liquid to a solid. This change of state results in a change of the phase angle measured for the gel. The phase angle reduces as the solution solidifies. This solidification is associated with an increase in the measured viscosity. The results in Tables 1 & 2 show for examples 1 & 2 (Tables 1 & 2) that although the initial solution viscosities are different, there are similar percentage changes in the two solutions as the initial gelation occurs (35%+/−7% for example 1 and 37%+/−4% for example 2). The data in the tables that relate viscosity to time show that the gelation process continues for many minutes after the initial gel onset, resulting in a 166 fold increase in the viscosity of example 1 and a 28 fold increase in example 2 after 40 minutes.

TABLE 3

Shear modulus data for example 1

| Example 1 | Time to gel onset/s | Viscosity/Pa·s | | | Shear modulus/Pa | | | | |
|---|---|---|---|---|---|---|---|---|---|
| | | At gel | | | | | | | |
| | | Initial | onset | Increase % | Initial | 5 min | 10 min | 15 min | 20 min |
| | 15 | 3.23 | 4.22 | 31 | 37 | 75 | 671 | 2012 | 2385 |
| | 55 | 4.38 | 6.25 | 43 | 44 | 87 | 957 | 2522 | 3652 |
| | 59 | 8.13 | 10.63 | 31 | 56 | 93 | 708 | 1714 | 2534 |
| Average | 43 | 5.3 | 7.0 | 35 | 46 | 81.0 | 779 | 2083 | 2857 |
| St dev | 24 | 2.6 | 3.3 | 7 | 10 | 9 | 156 | 409 | 693 |

TABLE 4

Shear modulus data for example 2

| Example 2 | Time to gel onset/s | Viscosity/Pa·s | | | Shear modulus/Pa | | | | |
|---|---|---|---|---|---|---|---|---|---|
| | | At gel | | | | | | | |
| | | Initial | onset | Increase % | Initial | 5 min | 10 min | 15 min | 20 min |
| | 47 | 8.1 | 11.2 | 38 | 47 | 124 | 590 | 900 | 1009 |
| | 63 | 12.0 | 16.7 | 39 | 42 | 126 | 503 | 699 | 894 |
| | 65 | 15.6 | 20.6 | 32 | 93 | 186 | 652 | 913 | 4741 |

TABLE 4-continued

Shear modulus data for example 2

| Example 2 | Time to gel onset/s | Viscosity/Pa · s | | | Shear modulus/Pa | | | | |
|---|---|---|---|---|---|---|---|---|---|
| | | Initial | At gel onset | Increase % | Initial | 5 min | 10 min | 15 min | 20 min |
| Average | 58 | 11.9 | 16.2 | 37 | 61 | 125 | 582 | 837 | 1050 |
| St dev | 10 | 3.8 | 4.7 | 4 | 28 | 1 | 75 | 120 | 181 |

As described previously when the gel solution converts from a liquid to a solid, there is a change in the measured phase angle for the gel. These results (Tables 3 & 4) demonstrate that the initial gelation increases the modulus of the solution and that although the initial module of examples 1 & 2 are different, they both increase by similar percentages in the initial gelation (35%+/−7% for example 1 and 37%+/−4% for example 2). The data in Tables 3 & 4 that relate sample shear modulus to time, demonstrates that-the gelation process continues for many minutes after the initial gel onset. The gelation process resulting in a 62 fold increase in the viscosity of example 1 and a 17 fold increase in example 2 after 40 minutes.

What is claimed is:

1. A composition for the treatment of a wound or skin injury, which is in sprayable form prior to application to the wound or skin injury, comprising from 0.25% to 1.5% by weight of the composition of a gellan gum, the composition further comprising an active ingredient dissolved or dispersed in the composition, wherein the active ingredient is selected from the group consisting of hyaluronic acid, esterified hyaluronic acid, an antiseptic, an antifungal agent, an antibacterial agent, and mixtures thereof, the viscosity of said composition increasing such that once applied to a wound or skin injury an immobile gel is formed.

2. The composition of claim 1 wherein the active ingredient is dissolved or dispersed in an aqueous solution of gellan gum.

3. The composition of claim 1, wherein the active ingredient is present in an amount of 0.1% to 10% by weight of the composition.

4. The composition of claim 1, wherein the composition comprises from 0.5% to 1.0% of gellan gum by weight of the composition.

5. The composition of claim 1, wherein the composition has a viscosity of from 0.1 Pa.s to 12 Pa.s prior to application to the wound.

6. The composition of claim 1, wherein the composition develops a viscosity of from 13 Pa.s to 800 Pa.s once in contact with the wound.

7. The composition of claim 1 in a spray device, which on actuation, the spray device discharges a metered dose of the composition.

* * * * *